(12) United States Patent
Firooznia et al.

(10) Patent No.: US 8,470,884 B2
(45) Date of Patent: Jun. 25, 2013

(54) ALKENYL NAPHTHYLACETIC ACIDS

(71) Applicant: Hoffmann-La Roche Inc., Nutley, NJ (US)

(72) Inventors: Fariborz Firooznia, Florham Park, NJ (US); Tai-An Lin, Pequannock, NJ (US); Sung-Sau So, Verona, NJ (US); Achyutharao Sidduri, West Orange, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 13/657,961

(22) Filed: Oct. 23, 2012

(65) Prior Publication Data

US 2013/0116322 A1    May 9, 2013

Related U.S. Application Data

(60) Provisional application No. 61/557,455, filed on Nov. 9, 2011.

(51) Int. Cl.
*A01N 37/12* (2006.01)
*C07C 315/00* (2006.01)

(52) U.S. Cl.
USPC .......................... 514/562; 562/427

(58) Field of Classification Search
USPC .......................... 514/562; 562/427
See application file for complete search history.

(56) References Cited

U.S. PATENT DOCUMENTS

| | | | |
|---|---|---|---|
| 3,899,529 A | 8/1975 | Witzel | |
| 4,048,330 A * | 9/1977 | Fried et al. | 514/569 |
| 4,371,537 A | 2/1983 | Markley et al. | |
| 4,443,462 A | 4/1984 | Carr et al. | |
| 4,868,331 A | 9/1989 | Niewoehner et al. | |
| 4,888,359 A * | 12/1989 | Contos | 514/569 |
| 4,921,998 A | 5/1990 | Niewoehner et al. | |
| 5,424,481 A | 6/1995 | Hagen et al. | |
| 7,226,951 B2 | 6/2007 | Vasudevan et al. | |
| 2005/0014749 A1 | 1/2005 | Chen et al. | |
| 2006/0154965 A1 | 7/2006 | Harris et al. | |
| 2007/0161698 A1 | 7/2007 | Chien et al. | |
| 2010/0016368 A1 | 1/2010 | Chen et al. | |
| 2010/0016369 A1 | 1/2010 | Chen et al. | |
| 2010/0041713 A1 | 2/2010 | Firooznia et al. | |
| 2010/0041714 A1 | 2/2010 | Blanc et al. | |
| 2010/0041760 A1 | 2/2010 | Blanc et al. | |
| 2010/0125058 A1 | 5/2010 | Chen et al. | |
| 2010/0125061 A1 | 5/2010 | Firooznia et al. | |
| 2010/0137250 A1 | 6/2010 | Firooznia et al. | |

FOREIGN PATENT DOCUMENTS

| | | |
|---|---|---|
| DE | 4411856 | 1/1994 |
| EP | 0242518 | 10/1987 |
| EP | 0253257 | 1/1988 |
| EP | 0405602 | 1/1991 |
| EP | 0657422 | 6/1995 |
| EP | 1505061 | 2/2005 |
| EP | 1939175 | 7/2008 |
| EP | 2022793 | 2/2009 |
| WO | 92/01675 | 2/1992 |
| WO | 97/07099 | 2/1997 |
| WO | 00/16798 | 3/2000 |
| WO | 03/028755 | 4/2003 |
| WO | 03/087098 | 10/2003 |
| WO | 2004/002992 | 1/2004 |
| WO | 2005/040114 | 5/2005 |
| WO | 2005/054232 | 6/2005 |
| WO | 2006/032466 | 3/2006 |
| WO | 2006/034418 | 3/2006 |
| WO | 2006/036664 | 4/2006 |
| WO | 2006/091674 | 8/2006 |
| WO | 2007/028132 | 3/2007 |
| WO | 2007/138974 | 12/2007 |
| WO | 2007/146136 | 12/2007 |
| WO | 2008/078308 | 7/2008 |
| WO | 2010/055004 | 4/2010 |
| WO | 2010/055005 | 5/2010 |
| WO | 2010/055006 | 5/2010 |

OTHER PUBLICATIONS

Hayashi, N. et al., Org. Lett. 7:3093-3096 ( 2005).
Baldwin et al., Synlett. 11:853-855 ( 1993).
International Search Report for PCT/EP2009/064810 dated Feb. 3, 2010.
Hayashi, J. et al., Org. Lett. 6:4981-4983 ( 2004).
Kostenis et al., Trends in Molecule Medicine 12(4):148-158 (Apr. 2006).
Ulven et al., Current Topics in Medicinal Chemistry 6(13):1427-1444 ( 2006).
Li, J. et al., Bioorg. Med. Chem. 13:1805-1809 ( 2005).

(Continued)

*Primary Examiner* — Jafar Parsa

(57) ABSTRACT

The invention is concerned with the compounds of formula (I):

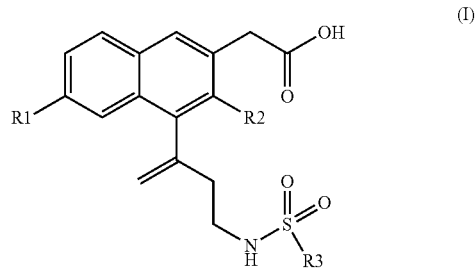

and pharmaceutically acceptable salts thereof, wherein R1, R2 and R3 are defined in the detailed description and claims. In addition, the present invention relates to methods of manufacturing and using the compounds of formula I as well as pharmaceutical compositions containing such compounds. The compounds of formula I are antagonists or partial agonists at the CRTH2 receptor and may be useful in treating diseases and disorders associated with that receptor such as asthma.

9 Claims, No Drawings

OTHER PUBLICATIONS

Liu, J. et al., Org. Lett. 4:3521-3524 (2002).
Bloomer, J.L. et al., J. Org. Chem. 58:7906-7912 (1993).
Blizzard, T.A. et al., Bioorg. Med. Chem. Lett. 14:3861-3864 (2004).
Thibault, M.E. et al., J. Org. Chem. 68:8373-8378 (2003).
(Opposition Notice filed to Corres Costa Rican Appl. 20112019 dated Nov. 29, 2011).
Kim, M. et al., J. Org. Chem. 69:6945-6948 (2004).
Testaferri, L. et al., Tetrahedron 41:1373-1384 (1985).
Schoen, U. et al., Tetrahedron Lett. 46:7111-7115 (2005).
International Search Report for PCT/EP2009/064816 dated Jan. 26, 2010.
Letter re: Thailand Office Action for Thai Patent Appl. No. 0901005108 (Jul. 11, 2011).
Uno, H. et al., J. Chem. Soc. 1:229 (2001).
Fuganti, C. et al., J. Chem. Res. (S):638-639 (1998).
Bargar, T.M. et al., J. Heterocyclic Chem. 22:1583-1592 (1985).
Xue, L. et al., Journal of Immunology 175:6531-6536 (2005).
Pettipher et al., Nature Reviews Drug Discovery 6:313-325 (Apr. 2007).
Wu, G. et al., Synthesis 11:1657-1660 (2003).
Huang et al., Hum. Mol. Genet. 13:2691-2697 (2004).
Zupan, M. et al., Bull. Chem. Soc. Jpn. 68:1655-1660 (1995).
Boger, D.L. et al., J. Org. Chem. 61:4894-4912 (1996).
Yoshimura-Uchiyama et al., Clin. Exp. Allergy 34:1283-1290 (2004).
Feixas et al., Bioorganic & Medicinal Chemistry Letter 11:2687-2690 (2001).
Chan, W.K. et al., J. Med. Chem. 39:3756-3768 (1996).
Moseley, J.D. et al., Tetrahedron 62:4685-4689 (2006).
Kozhinov, D.V. et al., J. Org. Chem. 69:1378-1379 (2004).
Hirai et al., J. Exp. Med 193:255-261 (2001).
Gervais et al., J. Allergy Clin. Immunol. 108:982-988 (2001).
(Translation of Chinese Off Act in Corres Chinese Appl 200980145703.0 Dec. 28, 2012).
Arnold et al., Org. Lett. 6:3005-3007 (2004).
International Search Report for PCT/EP2009/064813 dated Apr. 28, 2010.
Staas et al., Bioorg. Med. Chem. 14:6900-6916 (2006).
Cosmi et al., Eur. J. Immunol. 30:2972-2979 (2000).
Lee et al., Tetrahedron Lett. 32:5255 (1991).
Nagata et al., FEBS Lett 459:195-199 (1999).
Database Registry (Online) RN 1026178-75-5, XP002547292 (2008).
Wallace et al., Tetrahedron Lett. 43:6987-6990 (2002).
Trond et al., Exp. Opinion on Therap. Patents Informa 20(11):1505-1520 (2010).
Wei et al., Exp. Opinion on Invest. Drugs 14(7):769-773 (2005).
(International Search Report for PCT/EP2012/071871 Feb. 15, 2013).

* cited by examiner

ALKENYL NAPHTHYLACETIC ACIDS

PRIORITY TO RELATED APPLICATION(S)

This application claims the benefit of U.S. Provisional Application No. 61/557,455, filed Nov. 9, 2011, which is hereby incorporated by reference in its entirety.

RELATED APPLICATIONS

This application is related to U.S. application Ser. Nos. 12/614,485, filed Nov. 9, 2009; 12/614,478, filed Nov. 9, 2009; and 12/614,497, filed Nov. 9, 2009. The entire contents of these applications are expressly incorporated by reference herein.

BACKGROUND OF THE INVENTION

The present invention relates to novel substituted naphthalene-2-yl acetic acids, their manufacture, pharmaceutical compositions containing them and their use as CRTH2 antagonists, partial agonists, inverse agonists or partial inverse agonists.

Prostaglandin $D_2$ (PGD2) is the major prostanoid produced by activated mast cells and has been implicated in the pathogenesis of allergic diseases such as allergic asthma and atopic dermatitis. Chemoattractant Receptor-homologous molecule expressed on T-helper type cells (CRTH2) is one of the prostaglandin $D_2$ receptors and is expressed on the effector cells involved in allergic inflammation such as T helper type 2 (Th2) cells, eosinophils, and basophils (Nagata et al., *FEBS Lett* 459: 195-199, 1999). It has been shown to mediate PGD2-stimulated chemotaxis of Th2 cells, eosinophils, and basophils (Hirai et al., *J Exp Med* 193: 255-261, 2001). Moreover, CRTH2 mediates the respiratory burst and degranulation of eosinophils (Gervais et al., *J Allergy Clin Immunol* 108: 982-988, 2001), induces the production of proinflammatory cytokines in Th2 cells (Xue et al., *J Immunol* 175: 6531-6536), and enhances the release of histamine from basophils (Yoshimura-Uchiyama et al., *Clin Exp Aller* 34:1283-1290). Sequence variants of the gene encoding CRTH2, which differentially influence its mRNA stability, are shown to be associated with asthma (Huang et al., *Hum Mol Genet.* 13, 2691-2697, 2004). Increased numbers of circulating T cells expressing CRTH2 have also been correlated with severity of atopic dermatitis (Cosmi et al., *Eur J Immunol* 30, 2972-2979, 2000). These findings suggest that CRTH2 plays a proinflammatory role in allergic diseases. Therefore, antagonists of CRTH2 are believed to be useful for treating disorders such as asthma, allergic inflammation, COPD, allergic rhinitis, and atopic dermatitis.

SUMMARY OF THE INVENTION

The invention provides a compound of formula (I):

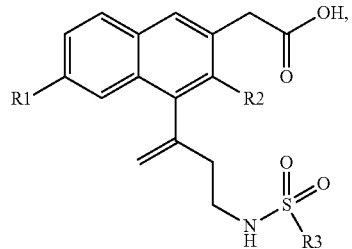

(I)

wherein:
R1 is halogen;
R2 is lower alkyl; and
R3 is cycloalkyl, unsubstituted phenyl or phenyl substituted with halogen,
or a pharmaceutically acceptable salt thereof.

The invention also provides for pharmaceutical compositions comprising the compounds, methods of using the compounds and methods of preparing the compounds.

All documents cited to or relied upon below are expressly incorporated herein by reference.

DETAILED DESCRIPTION OF THE INVENTION

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables $R^1$-$R^7$ of formula I refer to moieties that are attached to the core structure of formula I by a covalent bond.

In reference to a particular moiety with one or more hydrogen atoms, the term "substituted" refers to the fact that at least one of the hydrogen atoms of that moiety is replaced by another substituent or moiety. For example, the term "lower alkyl substituted by halogen" refers to the fact that one or more hydrogen atoms of a lower alkyl (as defined below) is replaced by one or more halogen atoms (e.g., trifluoromethyl, difluoromethyl, fluoromethyl, chloromethyl, etc.).

The term "optionally substituted" refers to the fact that one or more hydrogen atoms of a moiety (with one or more hydrogen atoms) can be, but does not necessarily have to be, substituted with another substituent.

The term "alkyl" refers to an aliphatic straight-chain or branched-chain saturated hydrocarbon moiety having 1 to 20 carbon atoms. In particular embodiments the alkyl has 1 to 10 carbon atoms.

The term "lower alkyl" refers to an alkyl moiety having 1 to 7 carbon atoms. In particular embodiments the lower alkyl has 1 to 4 carbon atoms and in other particular embodiments the lower alkyl has 1 to 3 carbon atoms. Examples of lower alkyls include methyl, ethyl, propyl, isopropyl, butyl, isobutyl, sec-butyl and tert-butyl.

"Aryl" means a monovalent cyclic aromatic hydrocarbon moiety having a mono-, bi- or tricyclic aromatic ring. The aryl group can be optionally substituted as defined herein. Examples of aryl moieties include, but are not limited to, phenyl, naphthyl, phenanthryl, fluorenyl, indenyl, pentalenyl, azulenyl, oxydiphenyl, biphenyl, methylenediphenyl, aminodiphenyl, diphenylsulfidyl, diphenylsulfonyl, diphenylisopropylidenyl, benzodioxanyl, benzofuranyl, benzodioxylyl, benzopyranyl, benzoxazinyl, benzoxazinonyl, benzopiperadinyl, benzopiperazinyl, benzopyrrolidinyl, benzomorpholinyl, methylenedioxyphenyl, ethylenedioxyphenyl, and the like, including partially hydrogenated derivatives thereof, each being optionally substituted.

The terms "halo", "halogen" and "halide", which may be used interchangeably, refer to a substituent fluoro, chloro, bromo, or iodo.

"Cycloalkyl" means a monovalent saturated carbocyclic moiety having mono- or bicyclic rings. The cycloalkyl moiety can optionally be substituted with one or more substituents. Examples of cycloalkyl moieties include, but are not limited to, cyclopropyl, cyclobutyl, cyclopentyl, cyclohexyl, cycloheptyl, and the like, including partially unsaturated (cycloalkenyl) derivatives thereof.

The term "halogen" refers to a moiety of fluoro, chloro, bromo or iodo.

Unless otherwise indicated, the term "hydrogen" or "hydro" refers to the moiety of a hydrogen atom (—H) and not $H_2$.

Unless otherwise indicated, the term "a compound of the formula" or "a compound of formula" or "compounds of the formula" or "compounds of formula" refers to any compound selected from the genus of compounds as defined by the formula (Including any pharmaceutically acceptable salt or ester of any such compound If not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like.

The compounds of the present invention can be present in the form of pharmaceutically acceptable salts. The compounds of the present invention can also be present in the form of pharmaceutically acceptable esters (i.e., the methyl and ethyl esters of the acids of formula Ito be used as prodrugs). The compounds of the present invention can also be solvated, i.e. hydrated. The solvation can be effected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the lower and upper limits may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

Useful pharmaceutical carriers for the preparation of the compositions hereof, can be solids, liquids or gases; thus, the compositions can take the form of tablets, pills, capsules, suppositories, powders, enterically coated or other protected formulations (e.g. binding on ion-exchange resins or packaging in lipid-protein vesicles), sustained release formulations, solutions, suspensions, elixirs, aerosols, and the like. The carrier can be selected from the various oils including those of petroleum, animal, vegetable or synthetic origin, e.g., peanut oil, soybean oil, mineral oil, sesame oil, and the like. Water, saline, aqueous dextrose, and glycols are preferred liquid carriers, particularly (when isotonic with the blood) for injectable solutions. For example, formulations for intravenous administration comprise sterile aqueous solutions of the active ingredient(s) which are prepared by dissolving solid active ingredient(s) in water to produce an aqueous solution, and rendering the solution sterile. Suitable pharmaceutical excipients include starch, cellulose, talc, glucose, lactose, talc, gelatin, malt, rice, flour, chalk, silica, magnesium stearate, sodium stearate, glycerol monostearate, sodium chloride, dried skim milk, glycerol, propylene glycol, water, ethanol, and the like. The compositions may be subjected to conventional pharmaceutical additives such as preservatives, stabilizing agents, wetting or emulsifying agents, salts for adjusting osmotic pressure, buffers and the like. Suitable pharmaceutical carriers and their formulation are described in Remington's Pharmaceutical Sciences by E. W. Martin. Such compositions will, in any event, contain an effective amount of the active compound together with a suitable carrier so as to prepare the proper dosage form for proper administration to the recipient.

In the practice of the method of the present invention, an effective amount of any one of the compounds of this invention or a combination of any of the compounds of this invention or a pharmaceutically acceptable salt or ester thereof, is administered via any of the usual and acceptable methods known in the art, either singly or in combination. The compounds or compositions can thus be administered orally (e.g., buccal cavity), sublingually, parenterally (e.g., intramuscularly, intravenously, or subcutaneously), rectally (e.g., by suppositories or washings), transdermally (e.g., skin electroporation) or by inhalation (e.g., by aerosol), and in the form of solid, liquid or gaseous dosages, including tablets and suspensions. The administration can be conducted in a single unit dosage form with continuous therapy or in a single dose therapy ad libitum. The therapeutic composition can also be in the form of an oil emulsion or dispersion in conjunction with a lipophilic salt such as pamoic acid, or in the form of a biodegradable sustained-release composition for subcutaneous or intramuscular administration.

In detail, the present invention provides for compounds of formula (I):

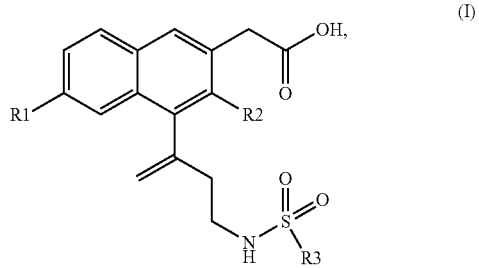

wherein:
R1 is halogen;
R2 is lower alkyl; and
R3 is cycloalkyl, unsubstituted phenyl or phenyl substituted with halogen,
or a pharmaceutically acceptable salt thereof.

In another embodiment, the invention provides for a compound according to formula (I), wherein R1 is fluorine.

In another embodiment, the invention provides for a compound according to formula (I), wherein R2 is methyl or ethyl.

In another embodiment, the invention provides for a compound according to formula (I), wherein R2 is methyl.

In another embodiment, the invention provides for a compound according to formula (I), wherein R3 is cyclohexyl.

In another embodiment, the invention provides for a compound according to formula (I), wherein R3 is chloro-phenyl.

In another embodiment, the invention provides for a compound according to formula (I), wherein the compound is:
{4-[3-(2-Chloro-benzenesulfonylamino)-1-methylene-propyl]-6-fluoro-3-methyl-naphthalen-2-yl}-acetic acid, or
[4-(3-Cyclohexanesulfonylamino-1-methylene-propyl)-6-fluoro-3-methyl-naphthalen-2-yl]-acetic acid.

In another embodiment, the invention provides for a pharmaceutical composition, comprising a therapeutically effective amount of a compound according to formula (I) and a pharmaceutically acceptable carrier.

In another embodiment, the invention provides for a compound according to formula (I) for use as a therapeutically active substance.

In another embodiment, the invention provides for the use of a compound according to formula (I) for the treatment or prophylaxis of a respiratory disorder.

In another embodiment, the invention provides for the use of a compound according to formula (I) for the preparation of a medicament for the treatment or prophylaxis of a respiratory disorder.

In another embodiment, the invention provides for a compound according to formula (I) for the treatment or prophylaxis of a respiratory disorder.

In another embodiment, the invention provides for a method for treating a respiratory disorder selected from chronic obstructive pulmonary disorder (COPD), asthma, and bronchospasm, comprising the step of administering a therapeutically effective amount of a compound according to formula (I) to a subject in need thereof.

In another embodiment, provided is an invention as hereinbefore described.

The starting materials and reagents used in preparing these compounds generally are either available from commercial suppliers, such as Aldrich Chemical Co., or are prepared by methods known to those skilled in the art following procedures set forth in references such as *Fieser and Fieser's Reagents for Organic Synthesis*; Wiley & Sons: New York, 1991, Volumes 1-15; *Rodd's Chemistry of Carbon Compounds*, Elsevier Science Publishers, 1989, Volumes 1-5 and Supplementals; and *Organic Reactions*, Wiley & Sons: New York, 1991, Volumes 1-40.

The following synthetic reaction schemes are merely illustrative of some methods by which the compounds of the present invention can be synthesized, and various modifications to these synthetic reaction schemes can be made and will be suggested to one skilled in the art having referred to the disclosure contained in this Application.

The starting materials and the intermediates of the synthetic reaction schemes can be isolated and purified if desired using conventional techniques, including but not limited to, filtration, distillation, crystallization, chromatography, and the like. Such materials can be characterized using conventional means, including physical constants and spectral data.

Unless specified to the contrary, the reactions described herein preferably are conducted under an inert atmosphere at atmospheric pressure at a reaction temperature range of from about −78° C. to about 150° C., more preferably from about 0° C. to about 125° C., and most preferably and conveniently at about room (or ambient) temperature, e.g., about 20° C.

Scheme 1

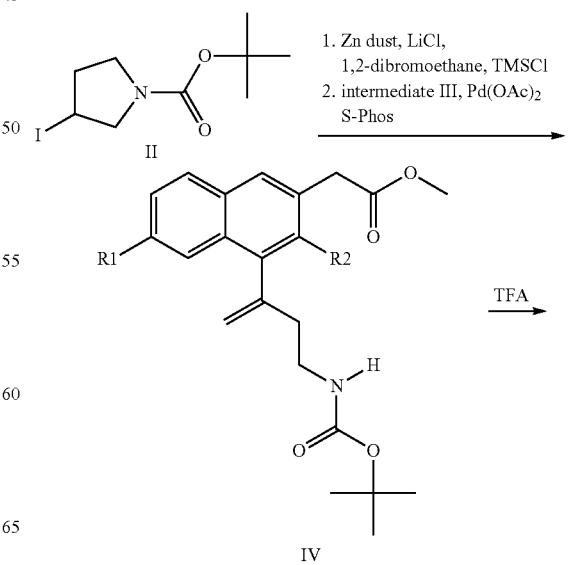

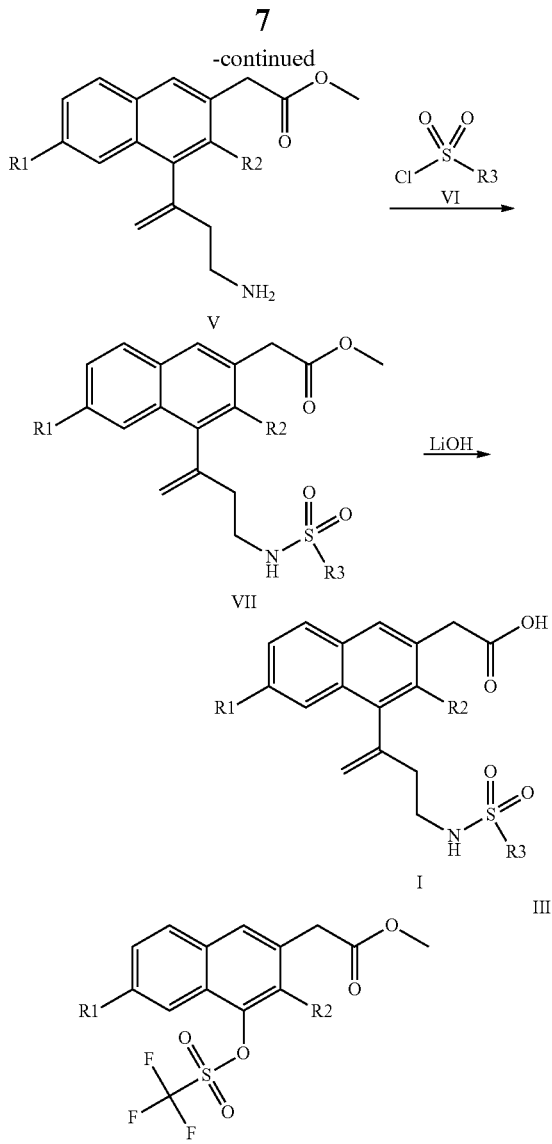

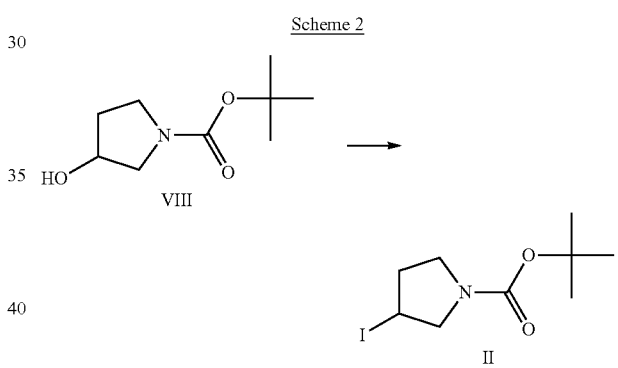

Deprotection of the tert-butyl carbamate group in IV to afford amine V can be carried out in the presence of an acid such as trifluoroacetic acid in a suitable solvent such as methylene chloride at room temperature for reaction times ranging from one to several hours (Lundt, B. F.; Johansen, N. L.; Volund, A.; Markussen, J. *International Journal of Peptide and Protein Research*, 12 (1978) 258).

The reaction of amine V with sulphonyl chlorides of type VI to provide compounds of type VII can be accomplished using methods that are well known to someone skilled in the art. For example, the reaction can be carried out in the presence of an amine base such as N,N-diisopropylethylamine in a suitable solvent such as tetrahydrofuran at temperatures between 0° C. and room temperature for reaction times ranging from two hours to 24 hours.

Hydrolysis of the methyl ester in VII to give the compounds of interest I can be readily accomplished using methods that are well known to someone skilled in the art. For example, the reactions can be carried out in the presence of an aqueous solution of base such as lithium hydroxide, in an inert solvent such as tetrahydrofuran, water, or mixtures thereof, at a temperature between room temperature and reflux temperature for several hours.

The 3-iodo-pyrrolidine-1-carboxylic acid tert-butyl ester intermediate II can be prepared according to Scheme 2.

Scheme 2

Starting with 3-iodo-pyrrolidine-1-carboxylic acid tert-butyl ester II, reaction with the naphthalene intermediate III affords compound IV. Deprotection of the tert-butyl carbamate generates the amine intermediate V. Reaction of V with sulfonyl chlorides of type VI furnishes compounds of type VII. Hydrolysis of the methyl ester affords the compounds of interest I. R1 can be, for example, halogen; R2 can be, for example, lower alkyl; and R3 can be, for example cycloalkyl, unsubstituted phenyl or phenyl substituted with halogen.

The reaction of 3-iodo-pyrrolidine-1-carboxylic acid tert-butyl ester II with the naphthalene intermediate III to form compound IV can be accomplished by first treating compound II with zinc dust and lithium chloride that was activated with 1,2-dibromoethane and chlorotrimethylsilane. This process can be carried out in an inert solvent such as tetrahydrofuran (THF) at temperatures between room temperature and 60° C. for several hours. The reagent thus formed can undergo a coupling reaction with intermediate III in the presence of a palladium catalyst such as palladium(II) acetate and a suitable phosphine ligand such as 2-dicyclohexylphosphino-2',6'-dimethoxybiphenyl (S-Phos). The reaction can be carried out in an inert solvent such as tetrahydrofuran (THF) at temperatures between 55° C. and 65° C. for reaction times ranging from 5 hours to 65 hours.

Starting with 3-hydroxy-pyrrolidine-1-carboxylic acid tert-butyl ester VIII, conversion of the hydroxyl group to an iodide affords 3-iodo-pyrrolidine-1-carboxylic acid tert-butyl ester II. This conversion can be carried out in the presence of iodine, triphenylphosphine, and imidazole in an inert solvent such as methylene chloride at room temperature for several hours (US 2010/0160280 A1).

The naphthalene intermediate III can be prepared according to Scheme 3 (see U.S. application Ser. Nos. 12/614,485; 12/614,478; and 12/614,497).

Scheme 3

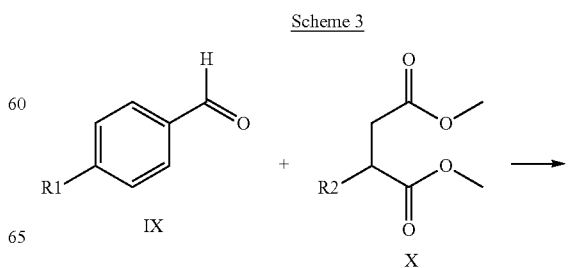

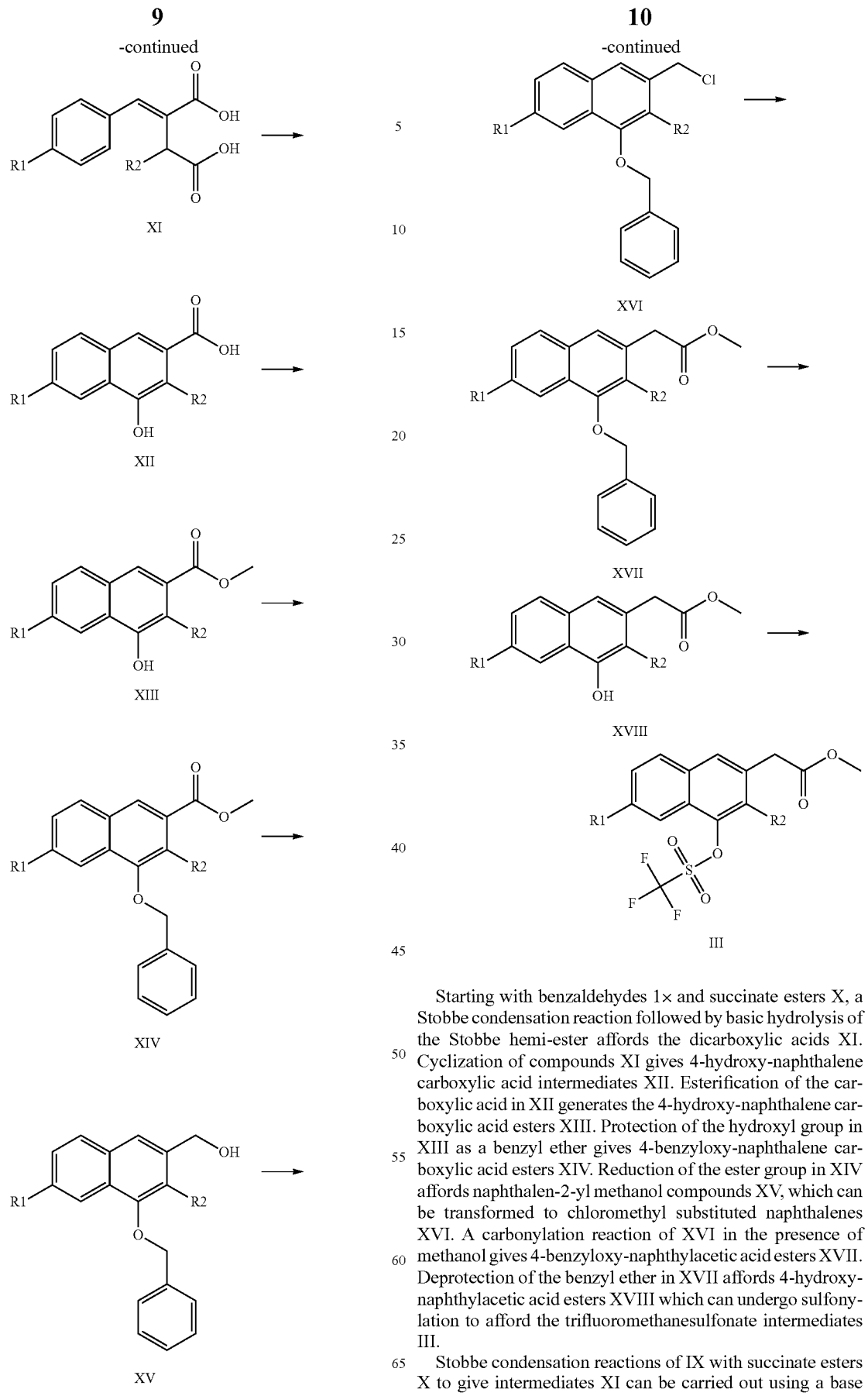

Starting with benzaldehydes 1x and succinate esters X, a Stobbe condensation reaction followed by basic hydrolysis of the Stobbe hemi-ester affords the dicarboxylic acids XI. Cyclization of compounds XI gives 4-hydroxy-naphthalene carboxylic acid intermediates XII. Esterification of the carboxylic acid in XII generates the 4-hydroxy-naphthalene carboxylic acid esters XIII. Protection of the hydroxyl group in XIII as a benzyl ether gives 4-benzyloxy-naphthalene carboxylic acid esters XIV. Reduction of the ester group in XIV affords naphthalen-2-yl methanol compounds XV, which can be transformed to chloromethyl substituted naphthalenes XVI. A carbonylation reaction of XVI in the presence of methanol gives 4-benzyloxy-naphthylacetic acid esters XVII. Deprotection of the benzyl ether in XVII affords 4-hydroxy-naphthylacetic acid esters XVIII which can undergo sulfonylation to afford the trifluoromethanesulfonate intermediates III.

Stobbe condensation reactions of IX with succinate esters X to give intermediates XI can be carried out using a base such as sodium methoxide, sodium ethoxide, potassium tertbutoxide, or sodium hydride in a suitable solvent such as methanol, ethanol, tert-butanol, toluene, benzene, or mixtures thereof, at temperatures between room temperature and 80° C. for one hour to several hours (Bloomer, J. L.; Stagliano, K. W.; Gazzillo, J. A. *J. Org. Chem.* 58 (1993) 7906). The resulting hemi-ester intermediates can readily undergo hydrolysis to afford the dicarboxylic acid intermediates XI. This reaction can be carried out in the presence of an aqueous solution of base such as sodium hydroxide or lithium hydroxide, in an inert solvent such as toluene, water, or mixtures thereof, at a temperature between room temperature and the reflux temperature for several hours.

Cyclization of the dicarboxylic acids XI to form 4-hydroxy-naphthalene carboxylic acids XII can be accomplished in neat trifluoromethanesulfonic acid at room temperature over several hours (Hong, W. P.; Lim, H. N.; Park, H. W.; Lee, K.-J. *Bull. Korean Chem. Soc.* 26 (2005) 655).

Intermediates XII can be readily converted to the 4-hydroxy-naphthalene carboxylic acid ester intermediates XIII in the presence of a catalytic amount of concentrated sulfuric acid and an alcohol solvent such as methanol or ethanol at temperatures between room temperature and 80° C. (or the reflux temperature) for several hours. Alternatively, the esterification reaction can be carried out in the presence of thionyl chloride and a suitable alcohol solvent such as methanol or ethanol at temperatures between 65° C. and 80° C. (or the reflux temperature) for several hours.

Preparation of intermediates XIV can be accomplished by treating XIII with benzyl chloride or benzyl bromide in the presence of a base such as potassium carbonate, sodium carbonate, or cesium carbonate. This reaction may occur in an inert organic solvent such as acetone, acetonitrile, or N,N-dimethylformamide at a temperature between room temperature and 80° C. for several hours.

Reduction of the ester group in XIV with lithium aluminum hydride gives the naphthalen-2-yl methanol compounds XV. This reaction can be carried out in an inert organic solvent such as tetrahydrofuran, diethyl ether, toluene, or mixtures thereof, at a temperature between 0° C. and 80° C. for several hours.

The chloromethyl naphthalene intermediates XVI can be prepared by the reaction of compounds XV with carbon tetrachloride and triphenylphosphine in an inert organic solvent such as toluene, acetonitrile, dichloromethane, N,N-dimethylformamide, or tetrahydrofuran at a temperature between 0° C. and 120° C. (or the reflux temperature) for several hours. Alternatively, the chlorination reaction may be accomplished using thionyl chloride either neat or in a suitable solvent such as dichloromethane, chloroform, N,N-dimethylformamide, benzene, or toluene at temperatures between 0° C. and 80° C. (or the reflux temperature) for several hours.

Conversion of chlorides XVI to the naphthylacetic acid esters XVII can be accomplished by a palladium catalyzed carbonylation reaction under one atmosphere of carbon monoxide in the presence of a base such as potassium carbonate in methanol and in the presence or absence of a co-solvent such as tetrahydrofuran. This transformation can be carried out using a palladium catalyst such as bis(triphenylphosphine) dichloropalladium(II) at a temperature between room temperature and 90° C. for 10 minutes to several hours (Schoenberg, A.; Bartoletti, I.; Heck, R. F. *J. Org. Chem.* 39 (1974) 3318).

Removal of the benzyl protecting group in XVII through catalytic hydrogenolysis affords the 4-hydroxy-naphthylacetic acid esters XVIII. This reaction can be carried out under one atmosphere of hydrogen in the presence of a catalyst such as 10% palladium on carbon or 20% palladium hydroxide on carbon in a solvent such as methanol or ethanol at room temperature for several hours. Alternatively, the benzyl ether can be removed in the presence of boron trifluoride diethyl etherate. This reaction can be performed in acetonitrile using sodium iodide as an additive at temperatures between 0° C. to room temperature for reaction times between one hour to several hours (Vankar, Y. D.; Rao, T. *J. Chem. Research (S)* (1985) 232).

Compounds XVIII can be converted to the trifluoromethanesulfonate esters III through a reaction with trifluoromethanesulfonic anhydride in the presence of an amine base such as pyridine, triethylamine, or diisopropylethylamine and in the presence or absence of an inert solvent such as dichloromethane for several hours at temperatures between 0° C. and room temperature.

EXAMPLES

Although certain exemplary embodiments are depicted and described herein, they should not be considered as limiting the scope of the invention, but merely as being illustrative and representative thereof. The compounds of the present invention can be prepared using appropriate starting materials according to the methods described generally herein and/or by methods available to one of ordinary skill in the art.

Intermediates and final compounds were purified by either flash chromatography and/or by reverse-phase preparative HPLC (high performance liquid chromatography). Unless otherwise noted, flash chromatography was performed using (1) the Biotage SP1™ system and the Quad 12/25 Cartridge module (from Biotage AB), (2) the ISCO CombiFlash® chromatography instrument (from Teledyne Isco, Inc.), or (3) an Analogix® IntelliFlash280™ chromatography instrument (from Analogix Inc., a subsidiary of Varian Inc.). Unless otherwise noted, the silica gel brand and pore size utilized were: (1) KP-SIL™ 60 Å, particle size: 40-60 micron (from Biotage AB); (2) Silica Gel CAS registry No: 63231-67-4, particle size: 47-60 micron; or (3) ZCX from Qingdao Haiyang Chemical Co., Ltd, pore size: 200-300 mesh or 300-400 mesh.

Mass spectrometry (MS) or high resolution mass spectrometry (HRMS) was performed using a Waters® ZQ™ 4000 (from Waters Corporation), a Waters® Quattro micro™ API (from Waters Corporation), a Micromass® Platform II (from Micromass, a division of Waters Corporation), a Bruker® Apex®II FTICR with a 4.7 Tesla magnet (from Bruker Corporation), a Waters® Alliance® 2795-ZQ™2000 (from Waters Corporation), or an MDS Sciex™ API-2000TMn API (from MDS Inc.). Mass spectra data generally only indicate the parent ions unless otherwise stated. MS or HRMS data is provided for a particular intermediate or compound where indicated.

Nuclear magnetic resonance spectroscopy (NMR) was performed using a Varian® Mercury300 NMR spectrometer (for the $^1$H NMR spectra acquired at 300 MHz), a Varian® Inova400 NMR spectrometer, a Bruker® 300 MHz NMR spectrometer, or a Bruker® 400 MHz NMR spectrometer. $^1$H NMR data is provided for a particular intermediate or compound where indicated.

All reactions involving air-sensitive reagents were performed under an inert atmosphere. Reagents were used as received from commercial suppliers unless otherwise noted.

Part I

Preparation of Starting Materials and Intermediates

Preparation of 3-iodo-pyrrolidine-1-carboxylic acid tert-butyl ester (Intermediate II)

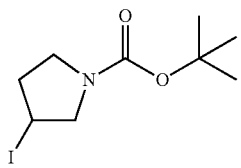

A round bottom flask was charged with 3-hydroxy-pyrrolidine-1-carboxylic acid tert-butyl ester (5.0 g, 0.027 mol), triphenylphosphine (10.5 g, 0.0401 mol), iodine (10.16 g, 0.0401 mol), imidazole (2.72 g, 0.0401 mol), and methylene chloride (90 mL). The reaction mixture was stirred at room temperature overnight. The reaction mixture was filtered, and the collected solids were washed with methylene chloride. The combined organic layers were concentrated. The resulting crude product was dissolved in ethyl acetate, and the organic phase was washed with water. The ethyl acetate layer was washed with a 3:1 mixture of water and methanol to remove triphenylphosphine oxide. The ethyl acetate layer was then washed with brine, dried over anhydrous MgSO$_4$, filtered, and concentrated. The crude product was loaded onto a 330 gram silica gel column. Flash chromatography afforded 3-iodo-pyrrolidine-1-carboxylic acid tert-butyl ester (6.9 g, 87%). $^1$H NMR (400 MHz, CDCl$_3$) δ ppm 4.31-4.42 (m, 1H), 3.84 (dd, J=12.60, 6.30 Hz, 1H), 3.67-3.79 (m, 1H), 3.54-3.64 (m, 1H), 3.40-3.49 (m, 1H), 2.20-2.32 (m, 2H), 1.48 (s, 8H). MS cald. for C$_5$H$_{71}$NO$_2$ [(M-C$_4$H$_9$)$^+$] 241, obsd. 241.7, 282.7 [(M-C$_4$H$_9$+41)$^+$].

Preparation of (6-fluoro-3-methyl-4-trifluoromethanesulfonyloxy-naphthalen-2-yl)-acetic acid methyl ester

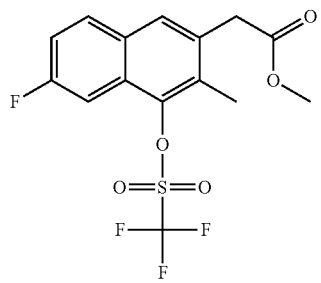 [SMILES: COC(=O)Cc1cc2ccc(F)cc2c(OS(=O)(=O)C(F)(F)F)c1C]

2-[1-(4-Fluoro-phenyl)-meth-(E)-ylidene]-3-methyl-succinic acid

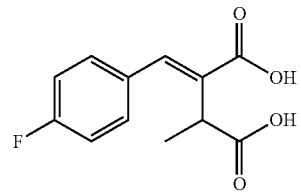 [SMILES: CC(C(=O)O)/C(=C\c1ccc(F)cc1)C(=O)O]

To a suspension of sodium hydride (60% in paraffin oil, 31g, 686 mmol) in toluene (150 mL) was added a solution of 4-fluorobenzaldehyde (30 g, 214 mmol) and dimethyl methylsuccinate (58 g, 312 mmol) in toluene (150 mL) over 1 hour at 0° C. under nitrogen. The reaction was initiated by addition of a drop of methanol at room temperature and was stirred at room temperature for 2 hours. The reaction was quenched by slow addition of 2.0 N aqueous NaOH (300 mL) at 0° C. The resulting mixture was stirred at 110° C. for 4 hours. The mixture was then cooled to room temperature and the aqueous layer was diluted with water (300 mL) and washed with Et$_2$O (2×300 mL). The aqueous phase was cooled in an ice-water bath. Addition of concentrated HCl was followed by extraction with ethyl acetate (2×100 mL). The combined organic extracts were washed with water (50 mL) followed by brine (50 mL). The organic phase was dried over anhydrous sodium sulfate and concentrated. The residue was crystallized from ethyl acetate-hexanes to give 2-[1-(4-fluoro-phenyl)-meth-(E)-ylidene]-3-methyl succinic acid. The procedure above was repeated using a separate amount of 4-fluorobenzaldehyde (30 g, 214 mmol). The products of the two reactions were combined to provide 2-[1-(4-fluoro-phenyl)-meth-(E)-ylidene]-3-methyl succinic acid as a pale yellow solid (28g, 27.5% overall). MS cald. for C$_{12}$H$_{12}$FO$_4$ [(M+H)$^+$]: 239, obsd. 239.2.

6-Fluoro-4-hydroxy-3-methyl-naphthalene-2-carboxylic acid

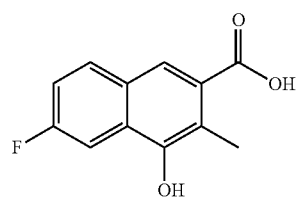 [SMILES: Cc1c(C(=O)O)cc2ccc(F)cc2c1O]

A solution of 2-[1-(4-fluoro-phenyl)-meth-(E)-ylidene]-3-methyl succinic acid (28 g, 119 mmol) in trifluoromethanesulfonic acid (140 mL) was stirred at room temperature for 16 h. The resulting mixture was carefully poured into ice cooled water with continuous stirring to obtain a solid precipitate, which was filtered, washed with water and dried in vacuo to yield 6-fluoro-4-hydroxy-3-methyl-naphthalene-2-carboxylic acid (28g, >100% crude) as yellow solid. This crude product was used in the next step without further purification. MS cald. for C$_{12}$H$_8$FO$_3$ [(M−H)$^+$]: 219, obsd. 218.9.

6-Fluoro-4-hydroxy-3-methyl-naphthalene-2-carboxylic acid methyl ester

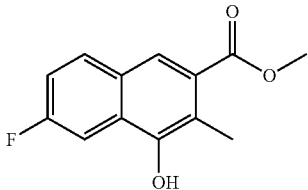 [SMILES: COC(=O)c1cc2ccc(F)cc2c(O)c1C]

To a 0° C. solution of 6-fluoro-4-hydroxy-3-methyl-naphthalene-2-carboxylic acid (28 g, 127 mmol) in MeOH (240 mL) was added concentrated sulfuric acid (18.9 mL, 382 mmol) dropwise. The reaction mixture was then warmed to room temperature and refluxed overnight. After this time, the methanol was distilled off under reduced pressure, and the crude mixture was diluted with ethyl acetate. This solution was washed with saturated aqueous $NaHCO_3$. The organic phase was dried over $Na_2SO_4$, filtered and concentrated under reduced pressure to give the crude product. Silica gel column chromatography (6% ethyl acetate-hexane) afforded 6-fluoro-4-hydroxy-3-methyl-naphthalene-2-carboxylic acid methyl ester (14.8 g, 50%) as light yellow solid. MS cald. for $C_{13}H_{12}FO_3$ $[(M+H)^+]$: 235, obsd. 235.2.

4-Benzyloxy-6-fluoro-3-methyl-naphthalene-2-carboxylic acid methyl ester

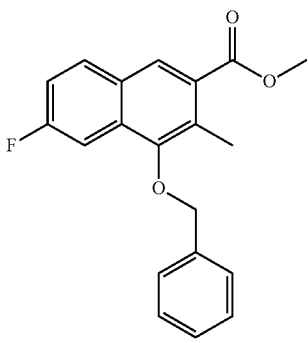 [SMILES: COC(=O)c1cc2ccc(F)cc2c(OCc2ccccc2)c1C]

To a solution of 6-fluoro-4-hydroxy-3-methyl-naphthalene-2-carboxylic acid methyl ester (21.7 g, 92.7 mmol) in dry DMF (250 mL) was added $K_2CO_3$ (17.9 g, 130 mmol), benzyl bromide (13 mL, 111 mmol) and $Bu_4NI$ (0.250 g) at room temperature under nitrogen. The reaction mixture was stirred for 3 hours at room temperature. The reaction mixture was diluted with water and extracted with ethyl acetate. The combined organic extracts were washed with water, brine, dried over anhydrous sodium sulfate and concentrated to give the crude product, which was purified using silica gel column chromatography (2-5% ethyl acetate-hexane) to yield 4-benzyloxy-6-fluoro-3-methyl-naphthalene-2-carboxylic acid methyl ester (25.4 g, 84%) as an off-white solid. MS cald. for $C_{20}H_{18}FO_3$ $[(M+H)^+]$: 325, obsd. 325.1.

(4-Benzyloxy-6-fluoro-3-methyl-naphthalen-2-yl)-methanol

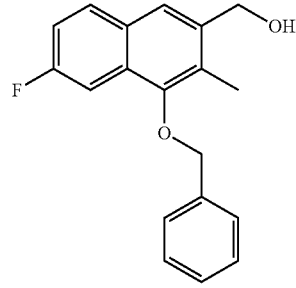 [SMILES: Cc1c(CO)cc2ccc(F)cc2c1OCc1ccccc1]

To a suspension of $LiAlH_4$ (8.8 g, 235 mmol) in dry THF (120 mL) was added a solution of 4-benzyloxy-6-fluoro-3-methyl-naphthalene-2-carboxylic acid methyl ester (25.4 g, 78.4 mmol) in THF (180 mL) dropwise at 0° C. under nitrogen. The reaction mixture was stirred at room temperature for 3 hours. After this time, the reaction mixture was cooled to 0° C. and quenched carefully via addition of cold water (10 mL) followed by 15% NaOH solution (10 mL) and additional water. The resulting solution was stirred for one hour, then filtered through a sintered glass funnel. The filter pad was washed with THF (50 mL). The combined filtrates were dried over $Na_2SO_4$, filtered, and concentrated to afford (4-benzyloxy-6-fluoro-3-methyl-naphthalen-2-yl)-methanol (21.5 g, 92%, crude) as a white solid. The crude product was used in the next step without further purification. MS cald. for $C_{19}H_{16}FO_2$ $[(M-H)^+]$: 295, obsd. 294.9.

1-Benzyloxy-3-chloromethyl-7-fluoro-2-methyl-naphthalene

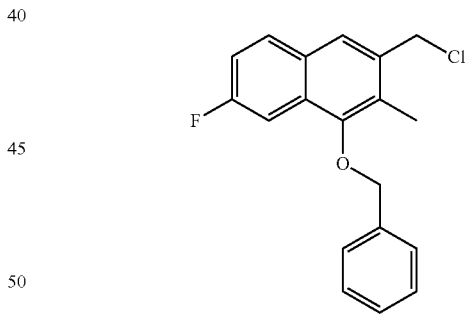

To a solution of triphenylphosphine (41.6 g, 159 mmol) in dry THF (190 mL) was added $CCl_4$ (59 mL). The reaction mixture was stirred for 10 minutes and (4-benzyloxy-6-fluoro-3-methyl-naphthalen-2-yl)-methanol (21.5 g, 79.4 mmol) was introduced as a solid at room temperature under nitrogen. The resulting solution was refluxed for 2 hours. The solvent was distilled off under reduced pressure, and the residue was diluted with water. The resulting mixture was extracted twice with ethyl acetate. The combined organic extracts were washed with water and brine, dried over anhydrous sodium sulfate, filtered, and concentrated. Silica gel column chromatography (100-200 mesh, 5% ethyl acetate in hexanes) provided 1-benzyloxy-3-chloromethyl-7-fluoro-2-methyl-naphthalene (18.5 g, 81%) as an off-white solid.

17
(4-Benzyloxy-6-fluoro-3-methyl-naphthalen-2-yl)-acetic acid methyl ester

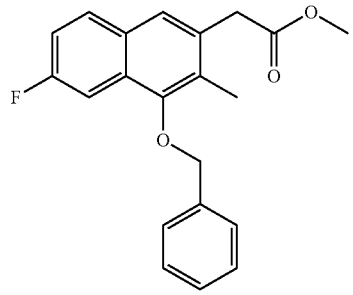 [SMILES: COC(=O)Cc1cc2ccc(F)cc2c(OCc2ccccc2)c1C]

To a stirred solution of 1-benzyloxy-3-chloromethyl-7-fluoro-2-methyl-naphthalene (18.5 g, 58.9 mmol) in a THF-methanol mixture (2:3; 500 mL) was added $K_2CO_3$ (8.94 g, 64.8 mmol) and $PdCl_2(PPh_3)_2$ (2.06 g, 2.96 mmol) at room temperature. The solution was degassed by purging with argon for 5 minutes. The reaction mixture was stirred under a balloon of carbon monoxide overnight at room temperature. After this time, the reaction progress was monitored by TLC (5% ethyl acetate in hexanes). The reaction mixture was concentrated, and the obtained crude residue was diluted with water and extracted with ethyl acetate. The combined organic extracts were washed with water and brine, dried over anhydrous sodium sulfate, filtered, and concentrated to give a crude product. Silica gel chromatography (100-200 mesh, 5% ethyl acetate-hexanes) yielded (4-benzyloxy-6-fluoro-3-methyl-naphthalen-2-yl)-acetic acid methyl ester (5.5 g, 97.8%) as a pale yellow solid. MS cald. for $C_{21}H_{20}FO_3$ [(M+H)$^+$]: 339, obsd. 339.0.

(6-Fluoro-4-hydroxy-3-methyl-naphthalen-2-yl)-acetic acid methyl ester

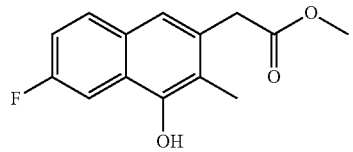 [SMILES: COC(=O)Cc1cc2ccc(F)cc2c(O)c1C]

To a stirred solution of (4-benzyloxy-6-fluoro-3-methyl-naphthalen-2-yl)-acetic acid methyl ester (15.8 g, 46.7 mmol) in MeOH (150 mL) was added 10% palladium on carbon (2.4 g). The resulting mixture was vigorously stirred under a balloon of hydrogen overnight. The reaction mixture was filtered through celite. The filtrate was concentrated to give the crude product, which was purified by silica gel chromatography (10% ethyl acetate in hexanes) to yield (6-fluoro-4-hydroxy-3-methyl-naphthalen-2-yl)-acetic acid methyl ester (9.5 g, 83%) as a white solid. MS cald. for $C_{14}H_{13}FO_3$ [(M+H)$^+$] 249, obsd. 249.1.

18
(6-Fluoro-3-methyl-4-trifluoromethanesulfonyloxy-naphthalen-2-yl)-acetic acid methyl ester

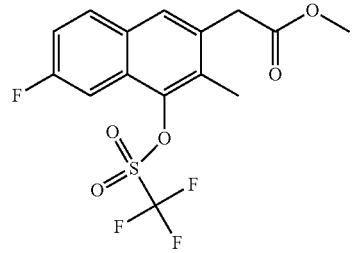 [SMILES: COC(=O)Cc1cc2ccc(F)cc2c(OS(=O)(=O)C(F)(F)F)c1C]

A light yellow solution of (6-fluoro-4-hydroxy-3-methyl-naphthalen-2-yl)-acetic acid methyl ester (12.2 g, 49.1 mmol) in methylene chloride (500 mL) was cooled to 0° C. using an ice-acetone bath. Pyridine (5.17 mL, 63.9 mmol) was added and then trifluoromethanesulfonic acid anhydride (20.8 g, 73.7 mmol) was added dropwise to the cold solution over 40 minutes. The resulting light yellow solution was stirred for two hours at 0° C. before being warmed to room temperature. The reaction mixture was stirred for another 30 minutes at room temperature. The mixture was quenched with water (300 mL) and the two layers were separated. The aqueous layer was extracted with dichloromethane (200 mL). The combined organic layers were washed with brine, dried over anhydrous $MgSO_4$, filtered, and concentrated to give the crude product as a light yellow solid. The crude product was dissolved in dichloromethane (~50 mL) with heating and then the mixture was diluted with hexanes (~100 mL). Some of the solvent was removed by heating with a heat gun. The resulting light brown solution was stored in the freezer for 15 hours. A white solid precipitated, which was collected by filtration and washed with hexanes. After air drying, (6-fluoro-3-methyl-4-trifluoromethanesulfonyloxy-naphthalen-2-yl)-acetic acid methyl ester (14.32 g, 77%) was isolated. $^1$H NMR (400 MHz, DMSO-d$_6$) δ ppm 7.83 (dd, J=9.03, 5.52 Hz, 1H), 7.75 (s, 1H), 7.65 (dd, J=10.29, 2.51 Hz, 1H), 7.31 (td, J=8.60, 2.38 Hz, 1H), 3.85 (s, 2H), 3.74 (s, 3H).

Preparation of [4-(3-amino-1-methylene-propyl)-6-fluoro-3-methyl-naphthalen-2-yl]-acetic acid methyl ester

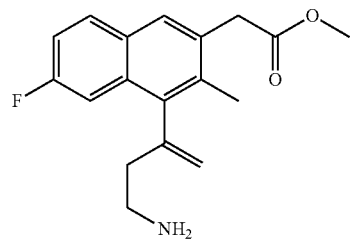 [SMILES: C=C(CCN)c1c(C)c(CC(=O)OC)cc2ccc(F)cc12]

Step 1: [4-(3-tert-butoxycarbonylamino-1-methyl-ene-propyl)-6-fluoro-3-methyl-naphthalen-2-yl]-acetic acid methyl ester

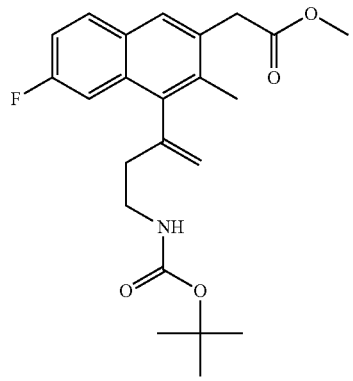 [SMILES: C=C(CCNC(=O)OC(C)(C)C)c1c(C)c(CC(=O)OC)cc2ccc(F)cc12]

To an oven-dried three neck round-bottom flask equipped with an addition funnel and a magnetic stir bar was added zinc (3.03 g, 46.4 mmol) and lithium chloride (1.96 g, 46.4 mmol). The solids were mixed together, and the reaction flask was placed under high vacuum. The flask was heated to 171° C., and the solids were stirred under high vacuum at this temperature for 1.5 hours. The mixture was cooled to room temperature, and the flask was back-filled with nitrogen gas. Tetrahydrofuran (THF) (3 mL) was added followed by 1,2-dibromoethane (0.40 mL, 4.6 mmol). The suspension was stirred and gently heated with a heat gun until gas evolution and foaming occurred. This process was repeated three times to completely activate the zinc. Chlorotrimethylsilane (0.59 mL, 4.6 mmol) was added and the suspension was stirred for 15 minutes at room temperature. A solution of 3-iodo-pyrrolidine-1-carboxylic acid tert-butyl ester (6.9 g, 23 mmol) in 15 mL THF was added dropwise. After addition of only 5 mL, the reaction temperature increased to 63° C., then the remaining iodide was added dropwise at ~50° C. for 10 minutes. The reaction mixture was heated to ~55° C. with heat gun and then the very thick reaction mixture was stirred for 3 hours. Tetrahydrofuran (10 mL) was added. Stirring was halted, and the suspension was allowed to settle, giving a clear solution above the unreacted zinc dust.

In a separate 3 neck round-bottom flask, palladium (II) acetate (0.26 g, 1.2 mmol), 2-dicyclohexylphosphino-2',6'-dimethoxybiphenyl (S-Phos) (0.95 g, 2.3 mmol), and THF (10 mL) were combined under nitrogen gas. A solution of 6-fluoro-3-methyl-4-trifluoromethanesulfonyloxy-naphthalen-2-yl)-acetic acid methyl ester (Intermediate III) (4.86 g, 12.8 mmol) in THF (10 mL) was added. The zinc solution from above was added to the reaction flask to form a brown solution. The reaction mixture was heated to 55° C. and stirred at this temperature over the weekend. After cooling to room temperature, the reaction mixture was poured into a solution of saturated ammonium chloride and brine solution. The organic compound was extracted into ethyl acetate (3×150 mL). The combined extracts were washed with brine solution and dried over anhydrous MgSO$_4$, filtered, and concentrated to provide 9.4 g of the crude product as an oil. The crude product was partially dissolved in acetonitrile (20 mL), producing some solids as a precipitate. The solids were collected by filtration and washed with acetonitrile. The filtrate was concentrated under vacuum to obtain a dark brown crude oil (8.9 g) which was purified using flash chromatography (330 g ISCO column, eluting with 100% hexanes ramped to 60% diethyl ether in hexanes). The third eluting product was [4-(3-tert-butoxycarbonylamino-1-methylene-propyl)-6-fluoro-3-methyl-naphthalen-2-yl]-acetic acid methyl ester (0.89 g, 9.6%). $^1$H NMR (400 MHz, CDCl$_3$) δ ppm 7.75 (dd, J=8.80, 5.80 Hz, 1H), 7.63 (s, 1H), 7.45 (dd, J=11.40, 2.50 Hz, 1H), 7.19 (td, J=8.70, 2.80 Hz, 1H), 5.60 (br. s, 1H), 5.09-5.12 (m, 1H), 3.82 (s, 2H), 3.73 (s, 3H), 3.26-3.34 (m, 2H), 2.53-2.59 (m, 2H), 2.37 (s, 3H), 1.43 (s, 8H).

Step 2: [4-(3-Amino-1-methylene-propyl)-6-fluoro-3-methyl-naphthalen-2-yl]-acetic acid methyl ester

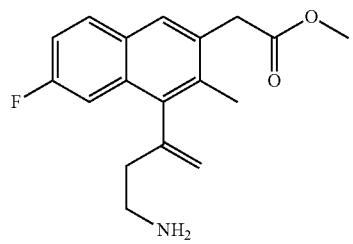 [SMILES: C=C(CCN)c1c(C)c(CC(=O)OC)cc2ccc(F)cc12]

To a solution of [4-(3-tert-butoxycarbonylamino-1-methylene-propyl)-6-fluoro-3-methyl-naphthalen-2-yl]-acetic acid methyl ester (0.79 g, 2.0 mmol) in methylene chloride (28.5 mL) was added trifluoroacetic acid (7.5 mL, 98 mmol). The reaction mixture was stirred at room temperature for 4 hours. The solvent was removed under vacuum and the resulting brown residue was dissolved in toluene. The solvent was again removed under vacuum, then dissolved in methylene chloride (~5 mL) with heating. The mixture was diluted with hexanes (~10 mL). As a result, some oil precipitated. The mixture was diluted with dichloromethane and the dark brown solution was stored in the refrigerator for 15 hours; however, further precipitation of the product was not successful. The solvent was removed and the crude mixture (1.1 g) was purified using flash chromatography (80 g ISCO column, 0-100% methylene chloride in hexanes followed by 0-20% methanol in methylene chloride) to afford [4-(3-amino-1-methylene-propyl)-6-fluoro-3-methyl-naphthalen-2-yl]-acetic acid methyl ester (0.502 g, 75%) as a white, amorphous, and hygroscopic solid. $^1$H NMR (400 MHz, CDCl$_3$) δ ppm 7.64-7.71 (m, 1H), 7.55-7.59 (m, 1H), 7.32-7.38 (m, 1H), 7.16 (td, J=8.5, 2.3 Hz, 1H), 5.53 (s, 1H), 5.09 (s, 1H), 3.77-3.81 (m, 2H), 3.67-3.71 (m, 4H), 2.99 (d, J=6.0 Hz, 2H), 2.65 (t, J=7.4 Hz, 2H), 2.28 (s, 4H).

Part II

Preparation of Certain Compounds of the Invention

Example 1

{4-[3-(2-Chloro-benzenesulfonylamino)-1-methylene-propyl]-6-fluoro-3-methyl-naphthalen-2-yl}-acetic acid

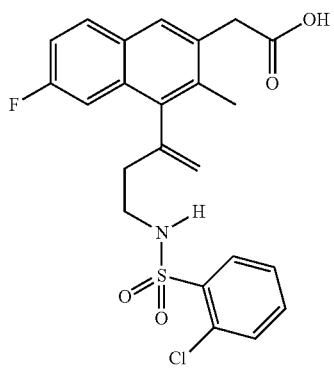 [SMILES: C=C(CCNS(=O)(=O)c1ccccc1Cl)c1c(C)c(CC(=O)O)cc2ccc(F)cc12]

Step 1: {4-[3-(2-Chloro-benzenesulfonylamino)-1-methylene-propyl]-6-fluoro-3-methyl-naphthalen-2-yl}-acetic acid methyl ester

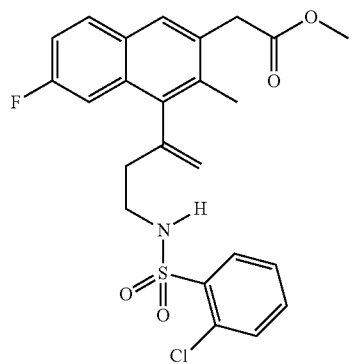 [SMILES: C=C(CCNS(=O)(=O)c1ccccc1Cl)c1c(C)c(CC(=O)OC)cc2ccc(F)cc12]

A solution of [4-(3-amino-1-methylene-propyl)-6-fluoro-3-methyl-naphthalen-2-yl]-acetic acid methyl ester (120 mg, 0.398 mmol) in THF (4 mL) was cooled to 0° C. and the solid 2-chlorobenzene-1-sulfonyl chloride (168 mg, 0.796 mmol) was added followed by N,N-diisopropylethylamine (154 mg, 209 µL, 1.19 mmol). After stirring for 2 hours at 0° C., the cooling bath was removed and the reaction mixture was warmed to room temperature. The reaction mixture was stirred at room temperature for 15 hours, then diluted with water and brine. The resulting mixture was extracted with ethyl acetate (2×50 mL). The combined organic layers were dried over MgSO$_4$, filtered, and concentrated to afford a viscous oil. Flash chromatography (40 g ISCO column, 100% hexanes ramped to 50% ethyl acetate in hexanes) provided {4-[3-(2-chloro-benzenesulfonylamino)-1-methylene-propyl]-6-fluoro-3-methyl-naphthalen-2-yl}-acetic acid methyl ester as a viscous oil. $^1$H NMR (400 MHz, CDCl$_3$) δ ppm 8.04-8.07 (m, 1H), 7.74 (dd, J=9.00, 5.80 Hz, 1H), 7.62 (s, 1H), 7.49-7.54 (m, 2H), 7.40 (dd, J=7.65, 2.89 Hz, 1H), 7.32 (dd, J=11.20, 2.60 Hz, 1H), 7.19 (td, J=8.60, 2.40 Hz, 1H), 5.52 (q, J=1.40 Hz, 1H), 5.08-5.10 (m, 1H), 5.03 (t, J=6.40 Hz, 1H), 3.80 (s, 2H), 3.73 (s, 3H), 3.09-3.16 (m, 2H), 2.51 (t, J=7.00 Hz, 2H), 2.31 (s, 3H). MS cald. for C$_{24}$H$_{24}$ClFNO$_4$S [(M+H)$^+$] 476.1, obsd. 476.1.

Step 2: {4-[3-(2-Chloro-benzenesulfonylamino)-1-methylene-propyl]-6-fluoro-3-methyl-naphthalen-2-yl}-acetic acid

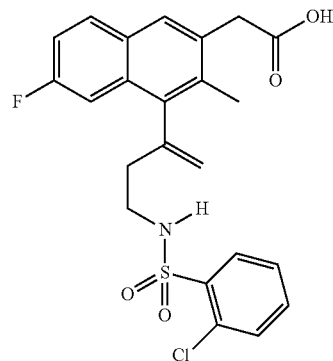

To a solution of {4-[3-(2-Chloro-benzenesulfonylamino)-1-methylene-propyl]-6-fluoro-3-methyl-naphthalen-2-yl}-acetic acid methyl ester (140 mg, 0.294 mmol) in THF (6 mL) was added a solution of LiOH (141 mg, 5.88 mmol) in water (1.5 mL). The resulting mixture was warmed with a heat gun to produce a clear solution, which was stirred for 15 hours at room temperature. At this time, LCMS analysis indicated the complete conversion of starting material. The THF was evaporated and the aqueous layer was diluted with water and slowly neutralized with 1.0 N HCl to obtain a white precipitate which was collected by filtration and washed with water and hexanes. After air drying, 125 mg of {4-[3-(2-chloro-benzenesulfonylamino)-1-methylene-propyl]-6-fluoro-3-methyl-naphthalen-2-yl}-acetic acid was isolated as an off-white solid. $^1$H NMR (400 MHz, DMSO-d$_6$) δ ppm 12.43 (bs, 1H), 7.96 (t, J=5.6 Hz, 1H), 7.87-7.93 (m, 2H), 7.73 (s, 1H), 7.59-7.62 (m, 2H), 7.45-7.51 (m, 1H), 7.29-7.38 (m, 2H), 5.50 (dd, J=3.3, 1.2 Hz, 1H), 4.93 (d, J=1.0 Hz, 1.2H), 3.72-3.80 (m, 2H), 3.00-3.12 (m, 2H), 2.30-2.39 (m, 2H), 2.17 (s, 3H). MS cald. for C$_{23}$H$_{22}$ClFNO$_4$S [(M+H)$^+$] 462.1, obsd. 462.0.

Example 2

[4-(3-Cyclohexanesulfonylamino-1-methylene-propyl)-6-fluoro-3-methyl-naphthalen-2-yl]-acetic acid

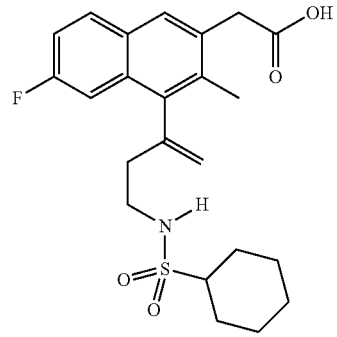 [SMILES: C=C(CCNS(=O)(=O)C1CCCCC1)c1c(C)c(CC(=O)O)cc2ccc(F)cc12]

[4-(3-Cyclohexanesulfonylamino-1-methylene-propyl)-6-fluoro-3-methyl-naphthalen-2-yf]-acetic acid was prepared according to the method described above for Example 1, starting from [4-(3-amino-1-methylene-propyl)-6-fluoro-3-methyl-naphthalen-2-yl]-acetic acid methyl ester and cyclohexanesulphonyl chloride. $^1$H NMR (400 MHz, CDCl$_3$) δ ppm 7.77 (dd, J=8.80, 6.00 Hz, 1H), 7.67 (s, 1H), 7.45 (dd, J=11.20, 2.60 Hz, 1H), 7.21 (td, J=8.60, 2.40 Hz, 1H), 5.61-5.63 (m, 1H), 5.12-5.15 (m, 1H), 4.04-4.10 (m, 1H), 3.87 (s, 2H), 3.28 (q, J=6.80 Hz, 2H), 2.65 (t, J=6.80 Hz, 2H), 2.40 (s, 3H), 1.79-1.88 (m, 4H), 1.64-1.72 (m, 4H), 1.36-1.47 (m, 4H). MS cald. for C$_{23}$H$_{27}$FNO$_4$S [(M−H)$^-$] 432.2, obsd. 432.2.

Example 3

DK-PGD$_2$-Induced IL-13 Production Assay in Th2 Cells

Inhibition of 13,14-dihydro-15-keto Prostaglandin D$_2$ (DK-PGD$_2$)-induced IL-13 production in T helper type 2 (Th2) cells was applied to evaluate compound cellular potency.

Cultures of Th2 cells were established from blood of healthy human volunteers according to the following procedure. Peripheral blood mononuclear cells (PBMC) were first isolated from 50 mL of fresh blood by Ficoll-Hypaque density gradient centrifugation, followed by CD4' cell purification using a CD4' T Cell Isolation Kit II (from Miltenyi Biotec Inc.). The CD4' T cells were then differentiated to Th2 cells by culturing the cells in X-VIVO 15® medium (from Cambrex BioScience Walkersville Inc.) containing 10% human AB serum (serum of blood type AB from Invitrogen Corporation), 50 U/mL of recombinant human interleukin-2 (rhIL-2) (from PeproTech Inc.) and 100 ng/mL of recombinant human interleukin-4 (rhIL-4) (from PeproTech Inc.) for 7 days. The Th2 cells were isolated using a CD294 (CRTH2) MicroBead Kit (from Miltenyi Biotec Inc.) and amplified in X-VIVO 15® medium containing 10% human AB serum and 50 U/mL of rhIL-2 for 2 to 5 weeks. In general, 70% to 80% of the Th2 cells used in the assay are CRTH2-positive when analyzed by fluorescence-activated cell sorting using the BM16 antibody (as previously described) conjugated to Alexa Fluor 647.

To determine cellular inhibitory potency, compounds at various concentrations were incubated with 2.5×10$^4$ Th2 cells and 500 nM DK-PGD$_2$ for 4 hrs at 37° C. in 200 L of X-VIVO 15® medium containing 10% human AB serum. IL-13 production to the medium was detected by ELISA (enzyme-linked immunosorbent assay) using an "Instant ELISA™" kit (from Bender MedSystems Inc.) according to the procedure suggested by the vendor. The spontaneous production of IL-13 by Th2 cells was determined in the absence of DK-PGD2 stimulation and the value was subtracted from that in the presence of each compound for percent inhibition and IC$_{50}$ calculations.

The percent inhibition of interleukin 13 (IL-13) production for a compound at various concentrations was calculated according to the following formula, [1−(IL-13 production in the presence of compound)/(IL-13 production in the presence of 0.15% DMSO)]$_{×100}$. The IC$_{50}$ value, defined as the concentration of a compound that is required for 50% inhibition of IL-13 production, was calculated by fitting the percent inhibition data for 7 concentrations to a sigmoidal dose-response (4 parameter logistic) model in the XLfit® software Excel add-in program [ID Business Solutions Ltd., model 205, where F(x)=(A+(B−A)/(1+((C/x)$^\wedge$D)))].

The compounds of interest were tested in the foregoing DK-PGD$_2$-induced IL-13 production assay. The results of the DK-PGD$_2$-induced IL-13 production are shown in the table below:

| Example Number | IC$_{50}$ (mM) |
|---|---|
| 1 | 0.0046 |
| 2 | 0.0144 |

It is to be understood that the invention is not limited to the particular embodiments of the invention described above, as variations of the particular embodiments may be made and still fall within the scope of the appended claims.

The invention claimed is:

1. A compound of formula (I):

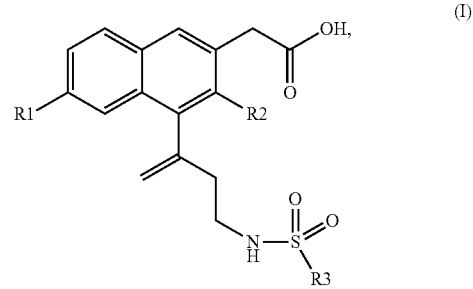

wherein:
R1 is halogen;
R2 is lower alkyl; and
R3 is cycloalkyl, unsubstituted phenyl or phenyl substituted with halogen,
or a pharmaceutically acceptable salt thereof.

2. The compound according to claim 1, wherein R1 is fluorine.

3. The compound according to claim 1, wherein R2 is methyl or ethyl.

4. The compound according to claim 1, wherein R2 is methyl.

5. The compound according to claim 1, wherein R3 is cyclohexyl.

6. The compound according to claim 1, wherein R3 is chloro-phenyl.

7. The compound according to claim 1, wherein said compound is:
{4-[3-(2-Chloro-benzenesulfonylamino)-1-methylene-propyl]-6-fluoro-3-methyl-naphthalen-2-yl}-acetic acid, or
[4-(3-Cyclohexanesulfonylamino-1-methylene-propyl)-6-fluoro-3-methyl-naphthalen-2-yl]-acetic acid.

8. A pharmaceutical composition, comprising a therapeutically effective amount of a compound according to claim 1 and a pharmaceutically acceptable carrier.

9. A method for treating a respiratory disorder selected from chronic obstructive pulmonary disorder (COPD), asthma, and bronchospasm, comprising the step of administering a therapeutically effective amount of a compound according to claim 1 to a subject in need thereof

* * * * *